(12) United States Patent
Lin

(10) Patent No.: US 10,806,828 B2
(45) Date of Patent: Oct. 20, 2020

(54) METHODS FOR REATTACHING DETACHED TISSUE TO HARD TISSUE USING BIOINDUCTIVE PATCH

(71) Applicant: DE NOVO ORTHOPEDICS INC., Taipei (TW)

(72) Inventor: Chia-Wei Lin, Kaohsiung (TW)

(73) Assignee: DE NOVO ORTHOPEDICS INC., Taipei (TW)

( * ) Notice: Subject to any disclaimer, the term of this patent is extended or adjusted under 35 U.S.C. 154(b) by 170 days.

(21) Appl. No.: 16/190,110

(22) Filed: Nov. 13, 2018

(65) Prior Publication Data

US 2019/0142409 A1  May 16, 2019

Related U.S. Application Data

(60) Provisional application No. 62/586,651, filed on Nov. 15, 2017.

(51) Int. Cl.
 *A61B 17/04* (2006.01)
 *A61L 27/58* (2006.01)
 (Continued)

(52) U.S. Cl.
 CPC .......... *A61L 27/58* (2013.01); *A61B 17/0401* (2013.01); *A61F 2/30756* (2013.01); *A61L 27/24* (2013.01); *A61L 27/34* (2013.01); *A61L 27/3604* (2013.01); *A61L 27/3662* (2013.01); *A61L 27/3691* (2013.01);
 (Continued)

(58) Field of Classification Search
 CPC ........ A61B 17/0401; A61B 2017/0404; A61B 2017/0406; A61B 2017/0414; A61B 2017/044; A61F 2/30756; A61F 2/0811–2002/0888; A61L 27/24; A61L 27/34; A61L 27/54; A61L 27/58;
 (Continued)

(56) References Cited

U.S. PATENT DOCUMENTS 8,900,620 B2 * 12/2014 Fulmer ............... A61M 31/002
424/426
2002/0161439 A1 * 10/2002 Strobel ................. A61F 2/0811
623/13.14

(Continued)

*Primary Examiner* — Kathleen S Holwerda
(74) *Attorney, Agent, or Firm* — WPAT, P.C., Intellectual Property Attorneys; Anthony King

(57) ABSTRACT

A method for reattaching a detached tissue to a hard tissue includes operation in which a suture anchor having a first stitch and a second stitch is provided, wherein the first stitch is divided into a first strand and a second strand, and the second stitch is divided into a third strand and a fourth strand. The suture anchor is fixed on a hard tissue. The first strand, the second strand, the third strand and the fourth strand pass through a detached tissue. A bioinductive patch is provided, wherein the bioinductive patch includes a patch body and a button. The first strand and the third strand pass through the patch body and a first suture hole of the button, and the second strand and the fourth strand pass through the patch body and a second suture hole of the button. The second strand and the third strand are knotted to form a first strand node, and the first strand node presses the bioinductive patch and the detached tissue tightly onto the hard tissue.

19 Claims, 15 Drawing Sheets

(51) Int. Cl.
*A61L 27/34* (2006.01)
*A61L 27/54* (2006.01)
*A61L 27/38* (2006.01)
*A61L 27/24* (2006.01)
*A61F 2/30* (2006.01)
*A61L 27/36* (2006.01)
*A61K 31/765* (2006.01)
*A61F 2/28* (2006.01)

(52) U.S. Cl.
CPC ........... *A61L 27/3843* (2013.01); *A61L 27/54* (2013.01); *A61B 2017/044* (2013.01); *A61B 2017/0404* (2013.01); *A61B 2017/0414* (2013.01); *A61F 2002/2817* (2013.01); *A61F 2002/30751* (2013.01); *A61F 2002/30761* (2013.01); *A61K 31/765* (2013.01); *A61L 2300/414* (2013.01)

(58) Field of Classification Search
CPC ............. A61L 27/3843; A61L 27/3604; A61L 27/3662; A61L 27/3691
USPC ........................................................ 606/232
See application file for complete search history.

(56) References Cited

U.S. PATENT DOCUMENTS

2003/0130694 A1* 7/2003 Bojarski ............... A61F 2/0805
606/228
2004/0030354 A1* 2/2004 Leung ................ A61B 17/0401
606/232

* cited by examiner

```
┌─────────────────────────────────────────────────────────┐
│ Provid a suture anchor, wherein the suture anchor has a stitch │
│ hole, a first stitch and a second stitch, the first stitch passes │
│ through the stitch hole and divided into a first strand and a   │── 101
│ second strand, and the second stitch passes through the stitch  │
│ hole and divided into a third strand and a fourth strand        │
└─────────────────────────────────────────────────────────┘
                            │
                            ▼
┌─────────────────────────────────────────────────────────┐
│           Fix the suture anchor on a hard tissue         │── 102
└─────────────────────────────────────────────────────────┘
                            │
                            ▼
┌─────────────────────────────────────────────────────────┐
│ Pass the first strand, the second strand, the third strand and the │── 103
│         fourth strand through a detached tissue                    │
└─────────────────────────────────────────────────────────┘
                            │
                            ▼
┌─────────────────────────────────────────────────────────┐
│ Provid a bioinductive patch, wherein the bioinductive patch      │
│ comprises a patch body and a button, the patch body has an       │
│ inner space, the button is disposed in the inner space of the    │── 104
│ patch body, and the button has a first suture hole and a second  │
│          suture hole spaced from each other                      │
└─────────────────────────────────────────────────────────┘
                            │
                            ▼
┌─────────────────────────────────────────────────────────┐
│ Pass the first strand and the third strand through the patch    │
│ body and the first suture hole of the button, and pass the      │── 105
│ second strand and the fourth strand through the patch body      │
│          and the second suture hole of the button               │
└─────────────────────────────────────────────────────────┘
                            │
                            ▼
┌─────────────────────────────────────────────────────────┐
│ Kont the second strand and the third strand to form a first    │
│ strand node, and the first strand node pressing the bioinductive│── 106
│     patch and the detached tissue tightly onto the hard tissue  │
└─────────────────────────────────────────────────────────┘
```

FIG. 1

METHODS FOR REATTACHING DETACHED TISSUE TO HARD TISSUE USING BIOINDUCTIVE PATCH

CROSS-REFERENCE TO RELATED APPLICATIONS

This application claims the benefit of U.S. Provisional Application No. 62/586,651, filed Nov. 15, 2017, the entire disclosure of which is incorporated by reference herein.

FIELD

The disclosure relates to a method for reattaching a detached tissue to a hard tissue, more particular to a method for reattaching a detached tissue to a hard tissue using a bioinductive patch.

BACKGROUND

Rotator cuff tear is one of the most common tendon disorders, which is often caused by chronic wear and tear with degeneration of the tendon. Rotator cuff tear can also occur in people who repeatedly perform overhead motions in their jobs or sports. According to statistics, approximately 13% of the population at an age greater than 50 suffers from rotator cuff tear, and over half of the population at an age greater than 80 is diagnosed with a rotator cuff tendon injury.

Treatment of the rotator cuff tear often includes surgical repair, but the rate of failure to gain or maintain healing has been reported to be as high as over 90%. This has been substantially attributed to the inadequate capacity of rotator cuff to heal once damaged. Scaffolds have been developed to improve rotator cuff-bone healing and rotator cuff regeneration, but not possess durable biological characteristics and ideal healing rate.

SUMMARY OF THE INVENTION

In accordance with one aspect of the present disclosure, a method for reattaching a detached tissue to a hard tissue includes operation in which a suture anchor is provided, wherein the suture anchor has a stitch hole, a first stitch and a second stitch, the first stitch passes through the stitch hole and divided into a first strand and a second strand, and the second stitch passes through the stitch hole and divided into a third strand and a fourth strand. The method continues with operation in which the suture anchor is fixed on a hard tissue. The method continues with operation in which the first strand, the second strand, the third strand and the fourth strand pass through a detached tissue. The method continues with operation in which a bioinductive patch is provided, wherein the bioinductive patch includes a patch body and a button, the patch body has an inner space, the button is disposed in the inner space of the patch body, and the button has a first suture hole and a second suture hole spaced from each other. The method continues with operation in which the first strand and the third strand pass through the patch body and the first suture hole of the button, and the second strand and the fourth strand pass through the patch body and the second suture hole of the button. The method continues with operation in which the second strand and the third strand are knotted to form a first strand node, and the first strand node presses the bioinductive patch and the detached tissue tightly onto the hard tissue.

BRIEF DESCRIPTION OF THE DRAWINGS

Aspects of the present disclosure are understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 1 is a flow diagram illustrating a method for reattaching a detached tissue to a hard tissue in accordance with some embodiments of the present disclosure.

DETAILED DESCRIPTION OF THE INVENTION

Figure 2A:
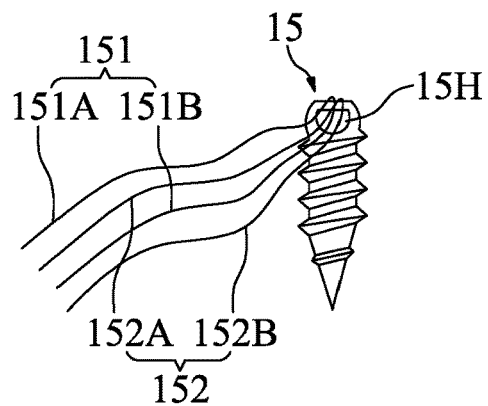
FIGS. 2A to 2I illustrate behavioral views of a method for reattaching a detached tissue to a hard tissue in various steps according to the present disclosure.

It is to be understood that the following disclosure provides many different embodiments or examples, for implementing different features of various embodiments. Specific examples of components and arrangements are described below to simplify the present disclosure. The present disclosure may, however, be embodied in many different forms and should not be construed as being limited to the embodiments set forth herein; rather, these embodiments are provided so that this description will be thorough and complete, and will fully convey the present disclosure to those of ordinary skill in the art. It will be apparent, however, that one or more embodiments may be practiced without these specific details.

In addition, the present disclosure may repeat reference numerals and/or letters in the various examples. This repetition is for the purpose of simplicity and clarity and does not in itself dictate a relationship between the various embodiments and/or configurations discussed.

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

Referring to FIG. 1, a method for reattaching a detached tissue to a hard tissue includes operation 101 in which a suture anchor is provided, wherein the suture anchor has a stitch hole, a first stitch and a second stitch, the first stitch passes through the stitch hole and divided into a first strand and a second strand, and the second stitch passes through the stitch hole and divided into a third strand and a fourth strand. The method continues with operation 102 in which the suture anchor is fixed on a hard tissue. The method continues with operation 103 in which the first strand, the second strand, the third strand and the fourth strand pass through a detached tissue. The method continues with operation 104 in which a bioinductive patch is provided, wherein the bioinductive patch includes a patch body and a button, the patch body has an inner space, the button is disposed in the inner space of the patch body, and the button has a first suture hole and a second suture hole spaced from each other. The method continues with operation 105 in which the first strand and the third strand pass through the patch body and the first suture hole of the button, and the second strand and the fourth strand pass through the patch body and the second suture hole of the button. The method continues with operation 106 in which the second strand and the third strand are knotted to form a first strand node, and the first strand node presses the bioinductive patch and the detached tissue tightly onto the hard tissue. The various operations of FIG. 1 are discussed below in more detail in association with behavioral views corresponding to the operations of the flow diagram. Although the operation sequence shown in FIG. 1 is 101, 102, 103, 104, 105 and 106, various operation sequences are within the contemplated scope of the present disclosure.

In FIG. 2A, a suture anchor 15 is provided. The suture anchor 15 has a stitch hole 15H, a first stitch 151 and a second stitch 152. The first stitch 151 passes through the stitch hole 15H and divided into a first strand 151A and a second strand 151B. The second stitch 152 passes through the stitch hole 15H and divided into a third strand 152A and a fourth strand 152B.

Figure 2B:
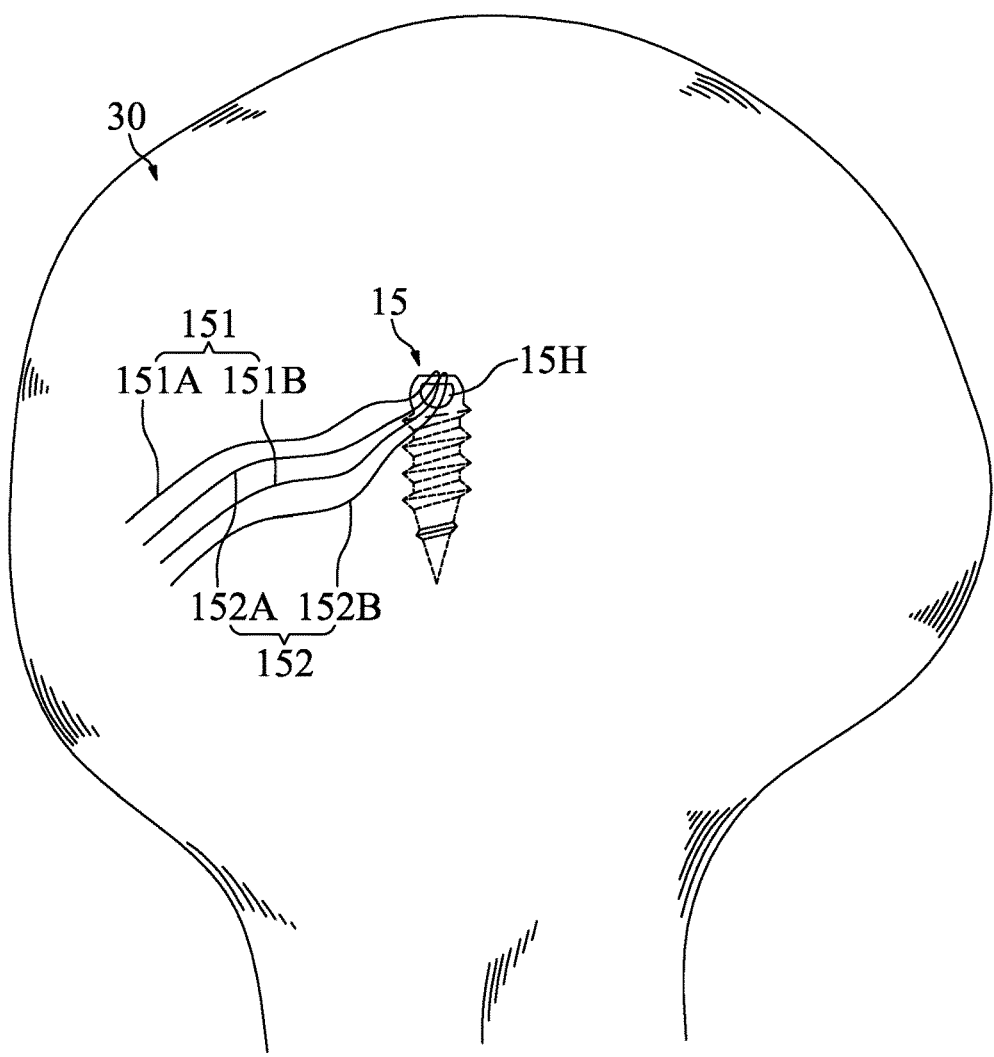

Referring to FIG. 2B, the suture anchor 15 is fixed on a hard tissue 30. In some embodiments, the hard tissue 30 is humerus.

Figure 2C:
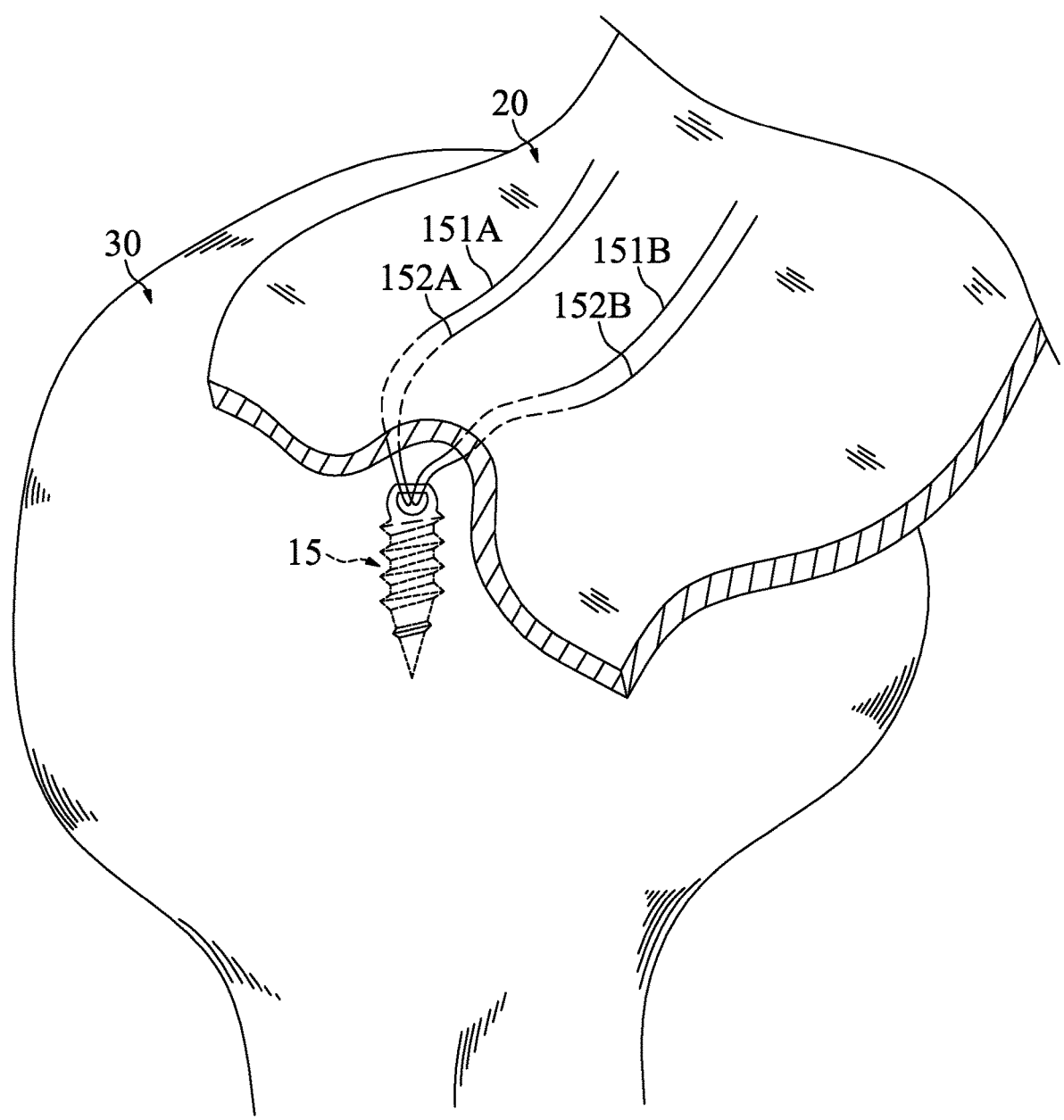

Referring to FIG. 2C, the first strand 151A, the second strand 151B, the third strand 152A and the fourth strand 152B pass through a detached tissue 20. In some embodiments, the detached tissue 20 is a soft tissue such as rotator cuff. In some embodiments, the detached tissue 20 can also be a hard tissue such as the bone chip.

Figure 2D:
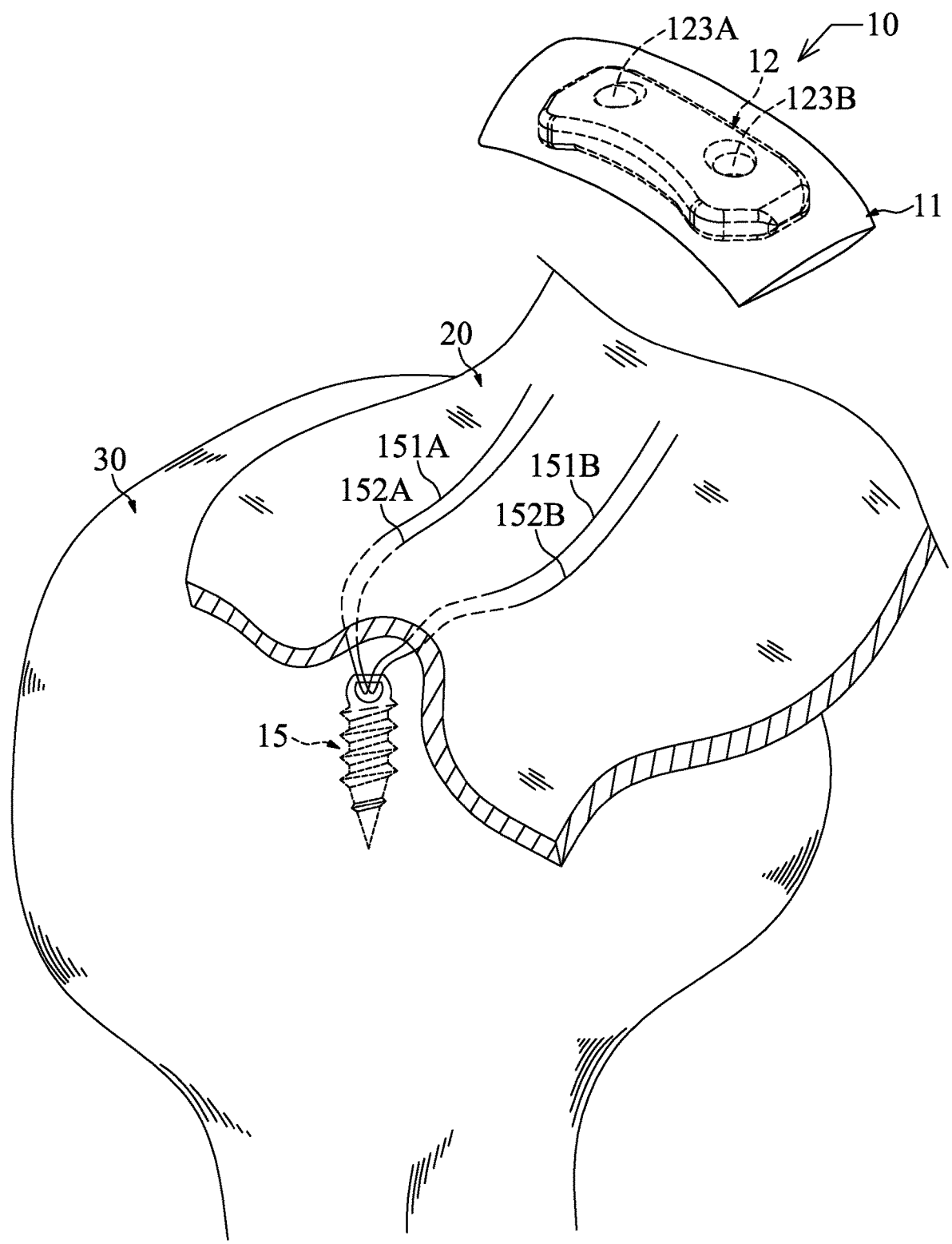
Figure 3:
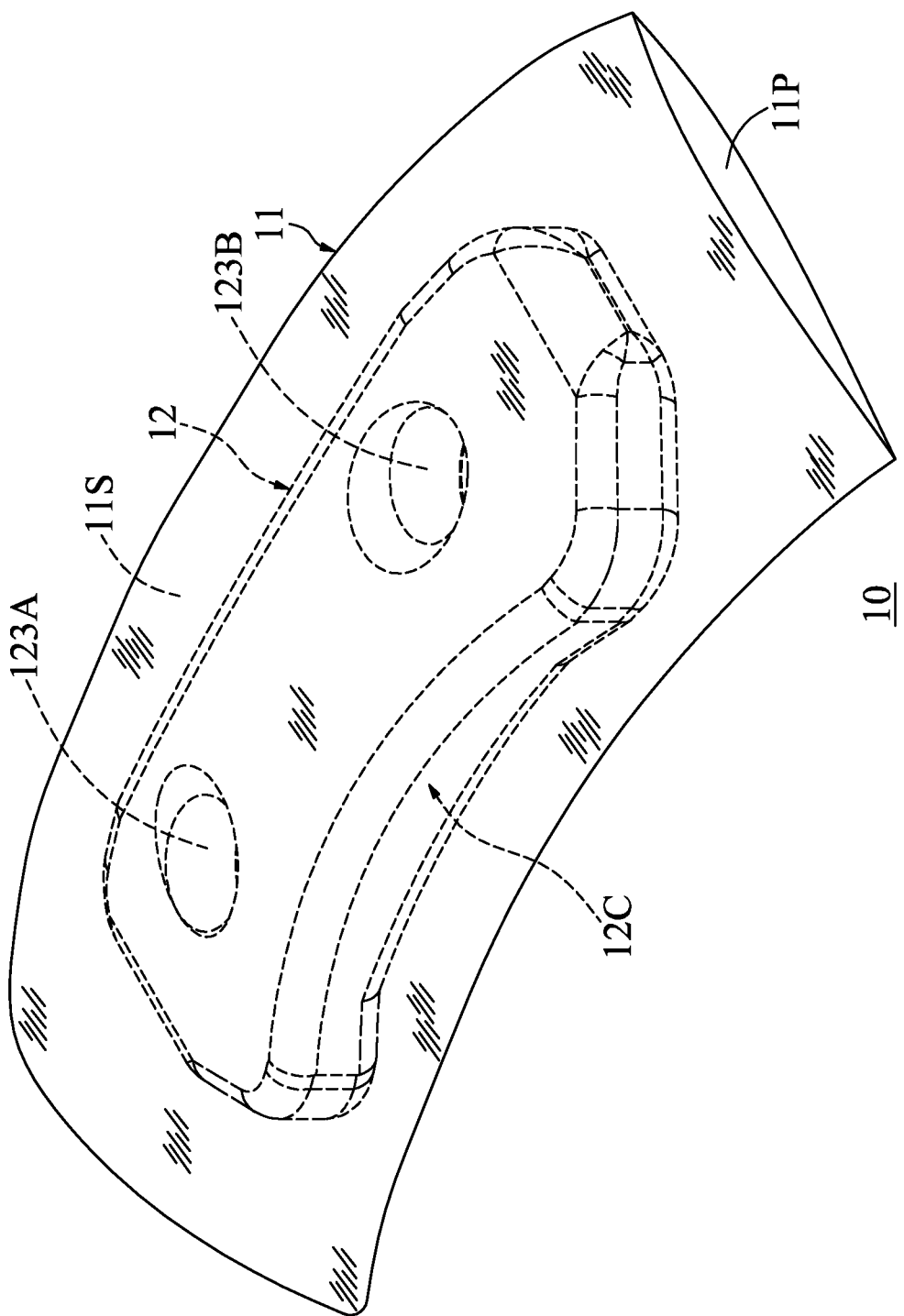
FIG. 3 is a perspective view of a bioinductive patch in accordance with some embodiments of the present disclosure.
Figure 4:
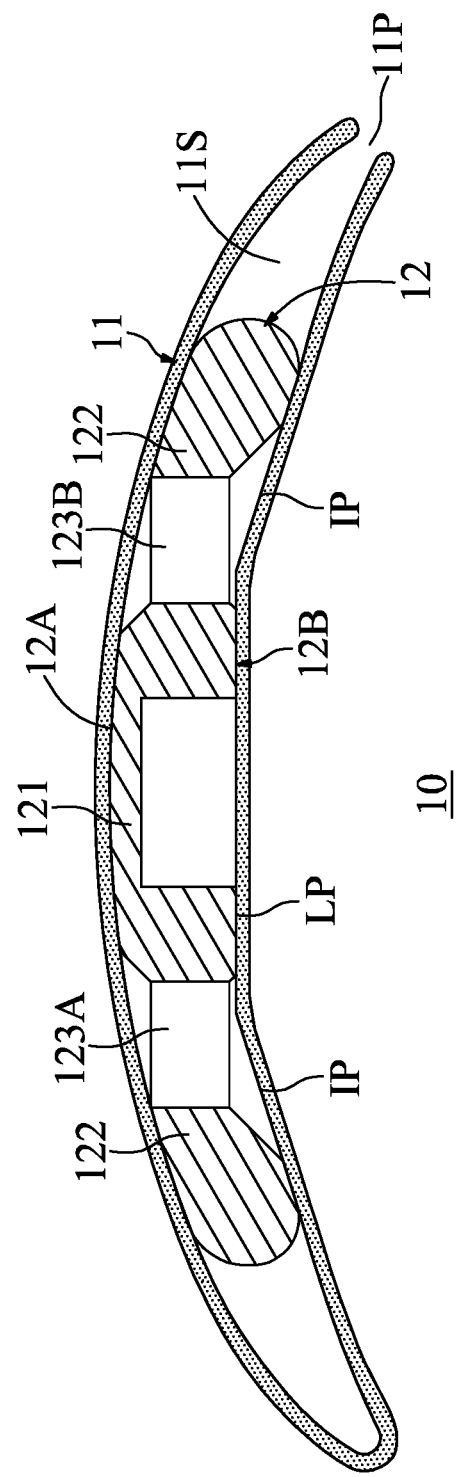
FIG. 4 is a cross-sectional view of a bioinductive patch in accordance with some embodiments of the present disclosure.

Referring to FIGS. 2D, 3 and 4, a bioinductive patch 10 is provided. The bioinductive patch 10 includes a patch body 11 and a button 12. The patch body 11 is made of bioabsorbable material. In some embodiments, the bioabsorbable material is decellularized collagen or amniotic membrane which can provide an environment that promotes the detached tissue 20 healing and regeneration.

The patch body 11 has an inner space 11S and an opening 11P. The inner space 11S is in communication with the opening 11P. In some embodiments, the patch body 11 is in envelope shape.

The button 12 is disposed in the inner space 11S of the patch body 11 through the opening 11P.

Figure 5:
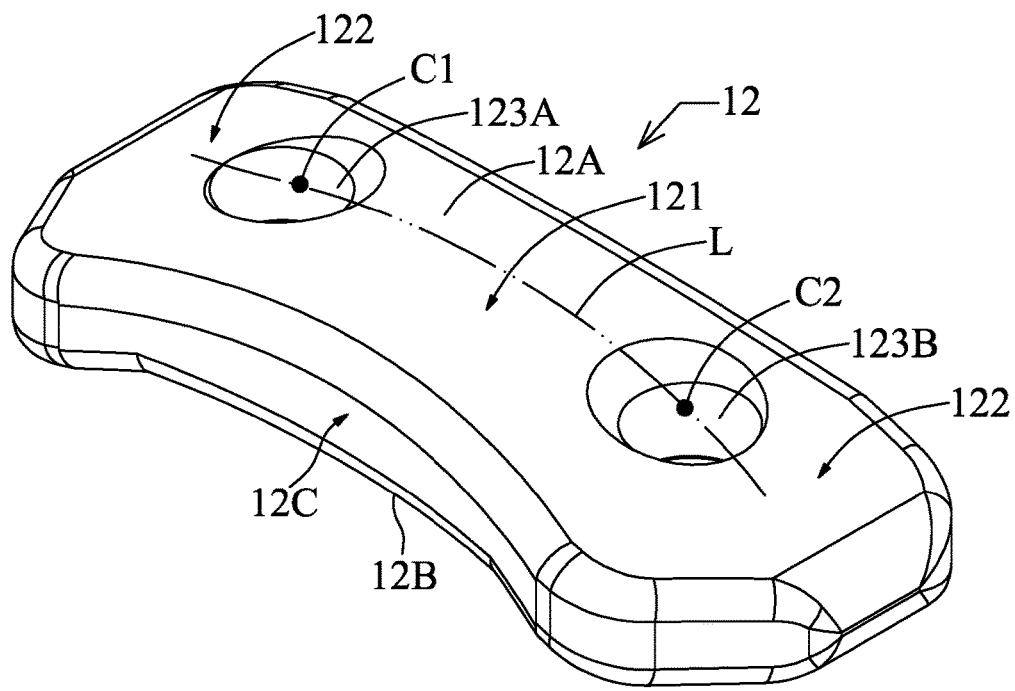
FIG. 5 is a perspective view of a button in accordance with some embodiments of the present disclosure.
Figure 6:
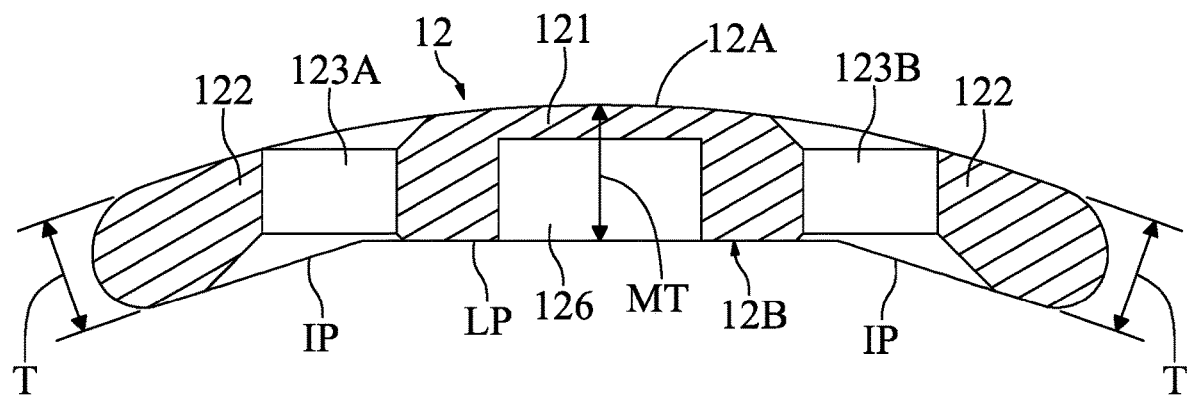
FIG. 6 is a cross-sectional view of a button in accordance with some embodiments of the present disclosure.

Referring to FIGS. 4, 5 and 6, the button 12 has a top surface 12A, a bottom surface 12B, a central portion 121, two side curved portions 122, a first suture hole 123A, a second suture hole 123B, a notch 12C, and a centerline L. The notch 12C corresponds to the central portion 121. The centerline L passes through a center C1 of the first suture hole 123A and a center C2 of the second suture hole 123B.

The top surface 12A contacts the patch body 11. In some embodiments, the top surface 12A is an arc surface to match the geometry of the hard tissue 30.

Figure 7:
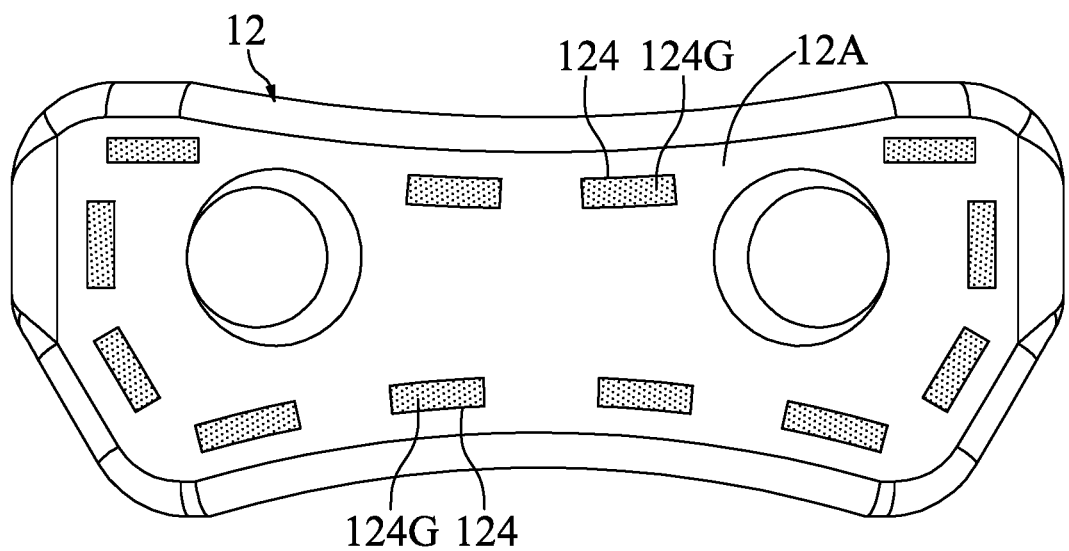
FIG. 7 is a top view of a button in accordance with some embodiments of the present disclosure.

Referring to FIGS. 4 and 7, in order to enhance the elasticity of the button 12, the button 12 can have a plurality of top cavities 124 formed on the top surface 12A. In some embodiments, the top cavities 124 can be disposed with at least one growth factor 124G. The growth factor 124G can be bonded and retained to the patch body 11.

Referring to FIGS. 4, 5 and 6 again, the bottom surface 12B contacts the patch body 11. In some embodiments, the bottom surface 12B includes a level plane LP and two inclined planes IP. The level plane LP is located at the central portion 121. The two inclined planes IP are located at two sides of the level plane LP, respectively.

Figure 8:
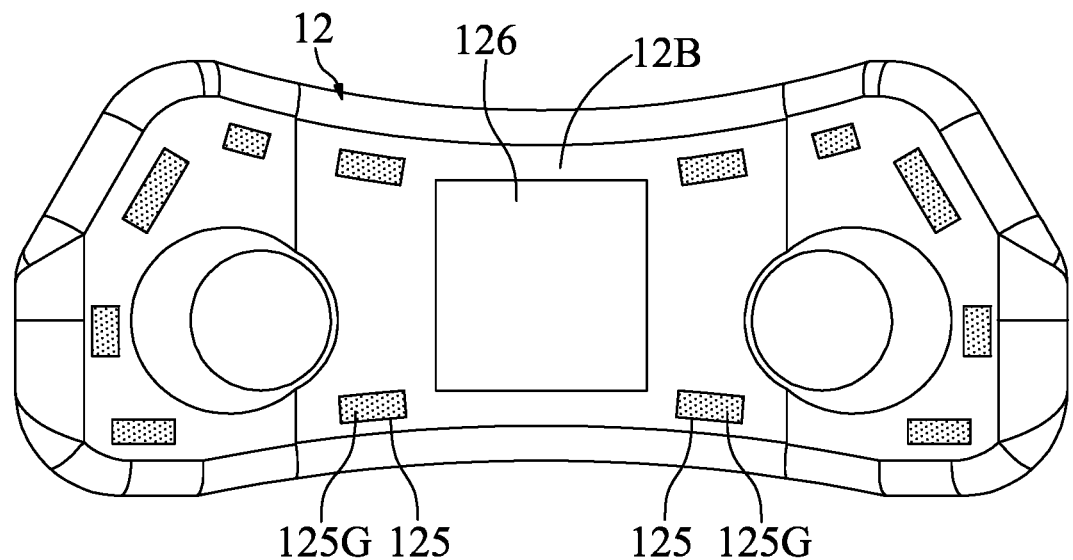
FIG. 8 is a bottom view of a button in accordance with some embodiments of the present disclosure.

Referring to FIGS. 4 and 8, in order to enhance the elasticity of the button 12, the button 12 can have a plurality of bottom cavities 125 formed on the bottom surface 12B. In some embodiments, the bottom cavities 125 can be disposed with at least one growth factor 125G. The growth factor 125G can bond to the patch body 11 and be retained inside the cavities.

Referring to FIG. 6 again, the central portion 121 has a center maximum thickness MT to increase overall stiffness and avoid breakage.

The two side curved portions 122 are connected to two sides of the central portion 121, respectively. In some embodiments, the center maximum thickness MT of the central portion 121 is greater than or equal to a thickness T of the side curved portion 122 to ensure that the button 12 can have a sufficient bending strength.

Referring to FIGS. 5 and 6 again, the first suture hole 123A and the second suture hole 123B are spaced from each other and are formed at the two side curved portions 122, respectively.

Figure 9:
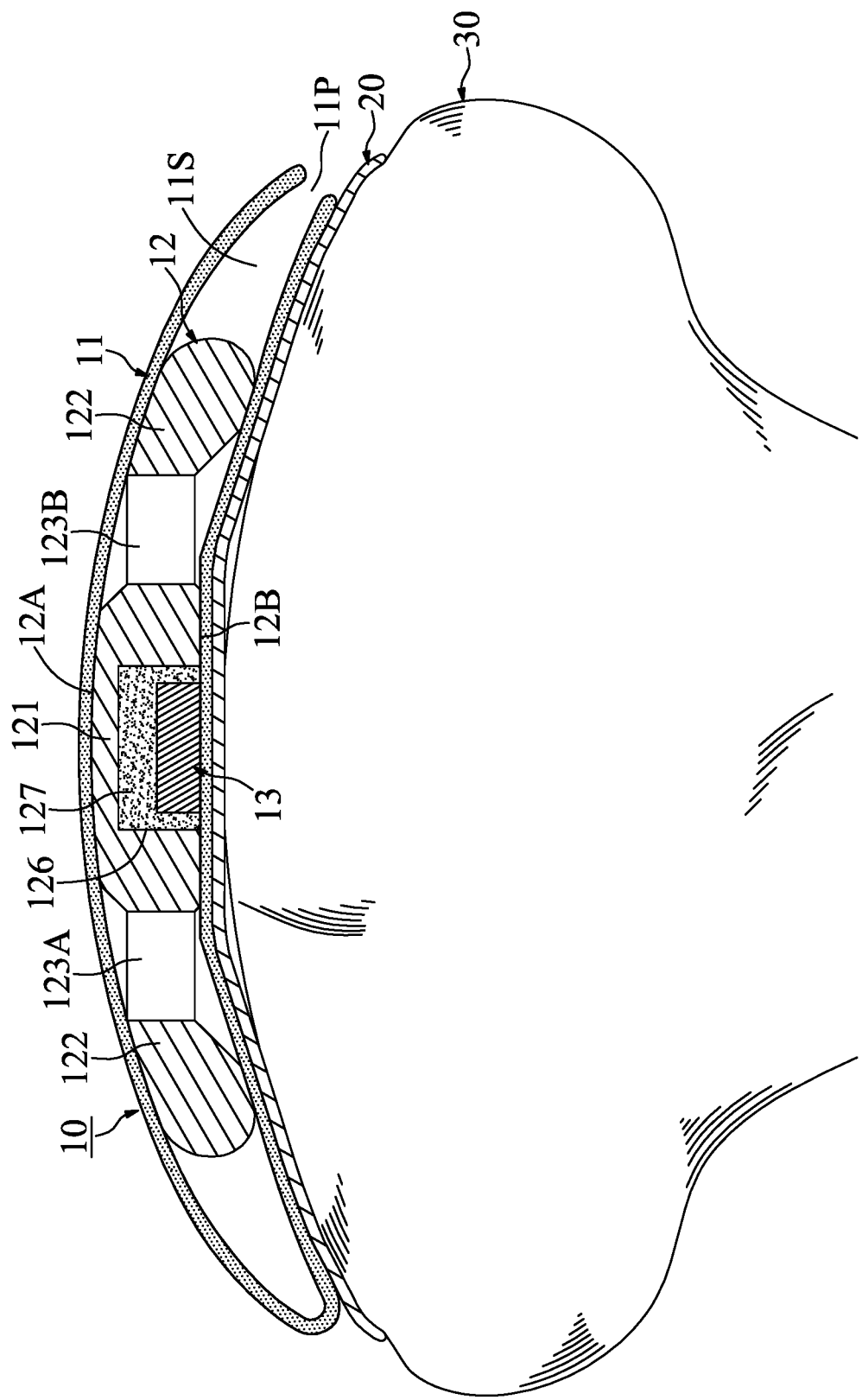
FIG. 9 illustrates a cross-sectional view of a bioinductive patch with a force sensor for reattaching a detached tissue to a hard tissue in accordance with some embodiments of the present disclosure.
Figure 10:
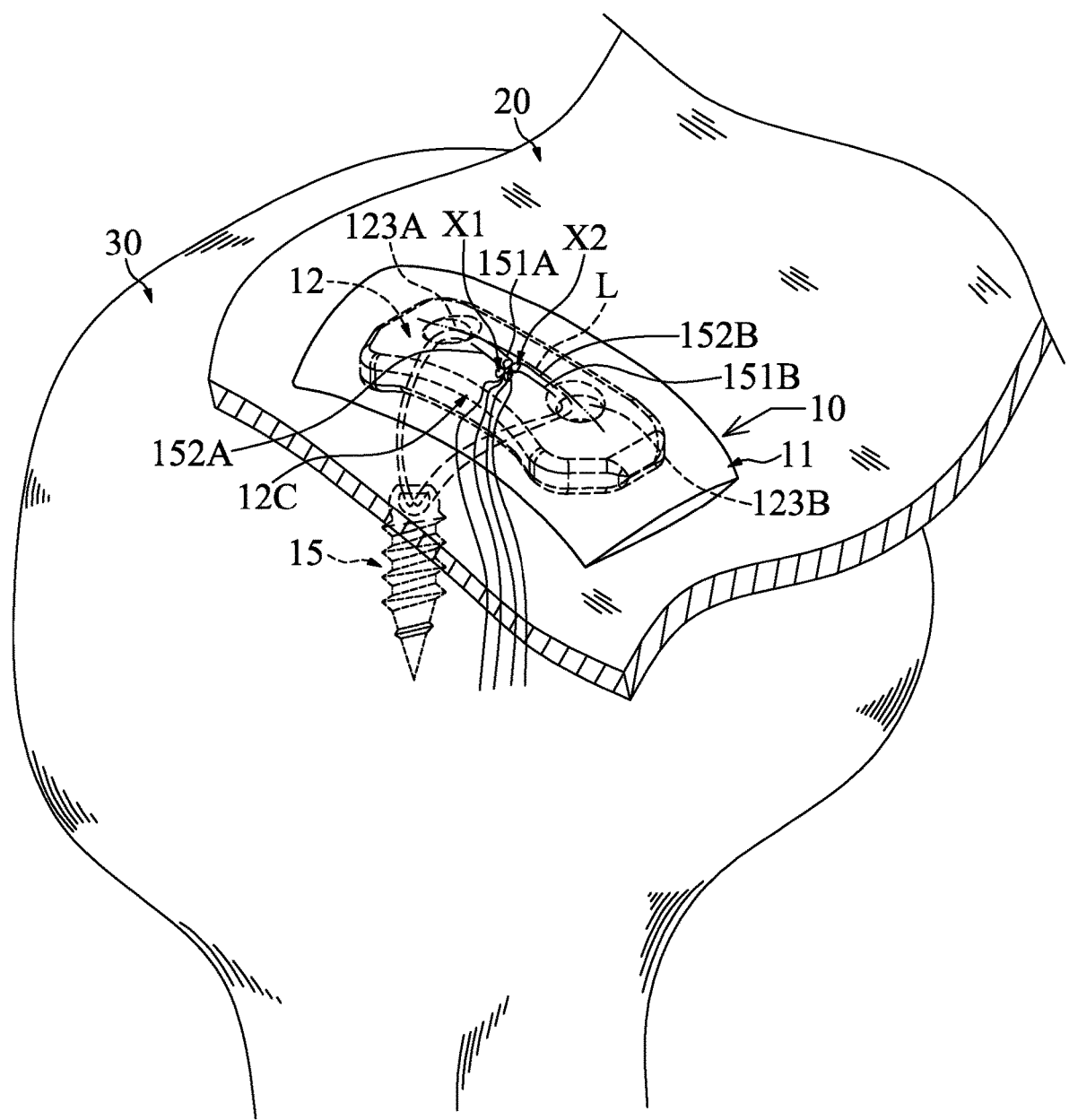
FIG. 10 illustrates behavioral view of knotting a first strand and a fourth strand to form a second strand node in accordance with some embodiments of the present disclosure.

Referring to FIGS. 2D and 9, a force sensor 13 can be disposed on the button 12 to detect a force variation between the button 12 and the detached tissue 20. The force sensor 13 can be pressure sensor, shear force sensor or tensile force sensor. Accordingly, the force variation can be pressure variation, shear force variation or tensile force variation.

In some embodiments, the button 12 has a bottom recession 126 dented from the bottom surface 12B and located at the central portion 121. The force sensor 13 is disposed in the bottom recession 126. Preferably, the force sensor 13 does not protrude from the bottom recession 126 to prevent the force sensor 13 interfering with the pressing effect between the button 12 and the detached tissue 20. In some embodiments, the bottom recession 126 can be filled with a sealing material 127 to seal the force sensor 13.

To improve the accuracy of the detected force variation, the force sensor 13 is located between the first suture hole 123A and the second suture hole 123B.

Figure 2E:
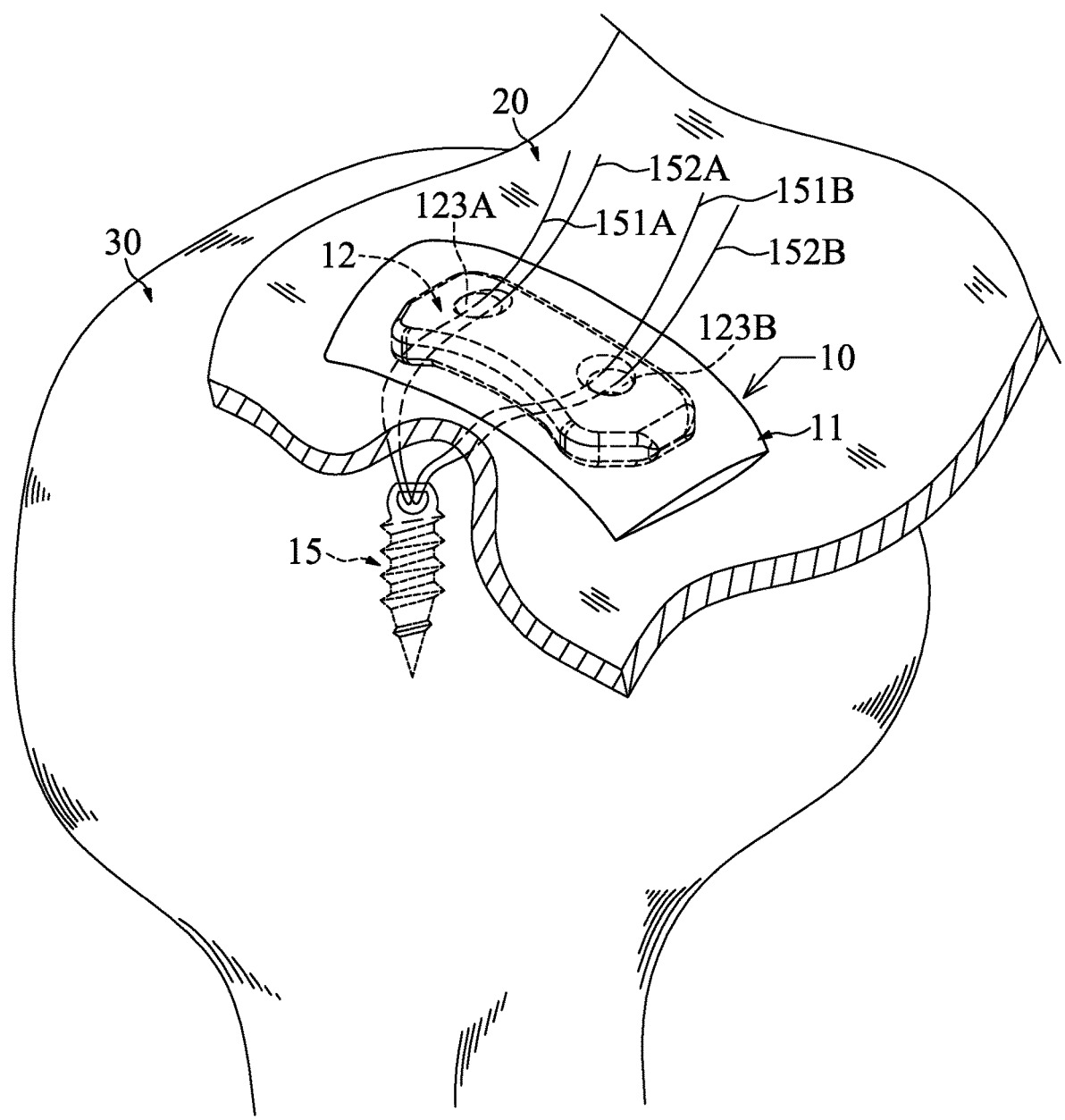

Referring to FIG. 2E, the first strand 151A and the third strand 152A pass through the patch body 11 and the first suture hole 123A of the button 12, and the second strand 151B and the fourth strand 152B pass through the patch body 11 and the second suture hole 123B of the button 12.

Figure 2F:
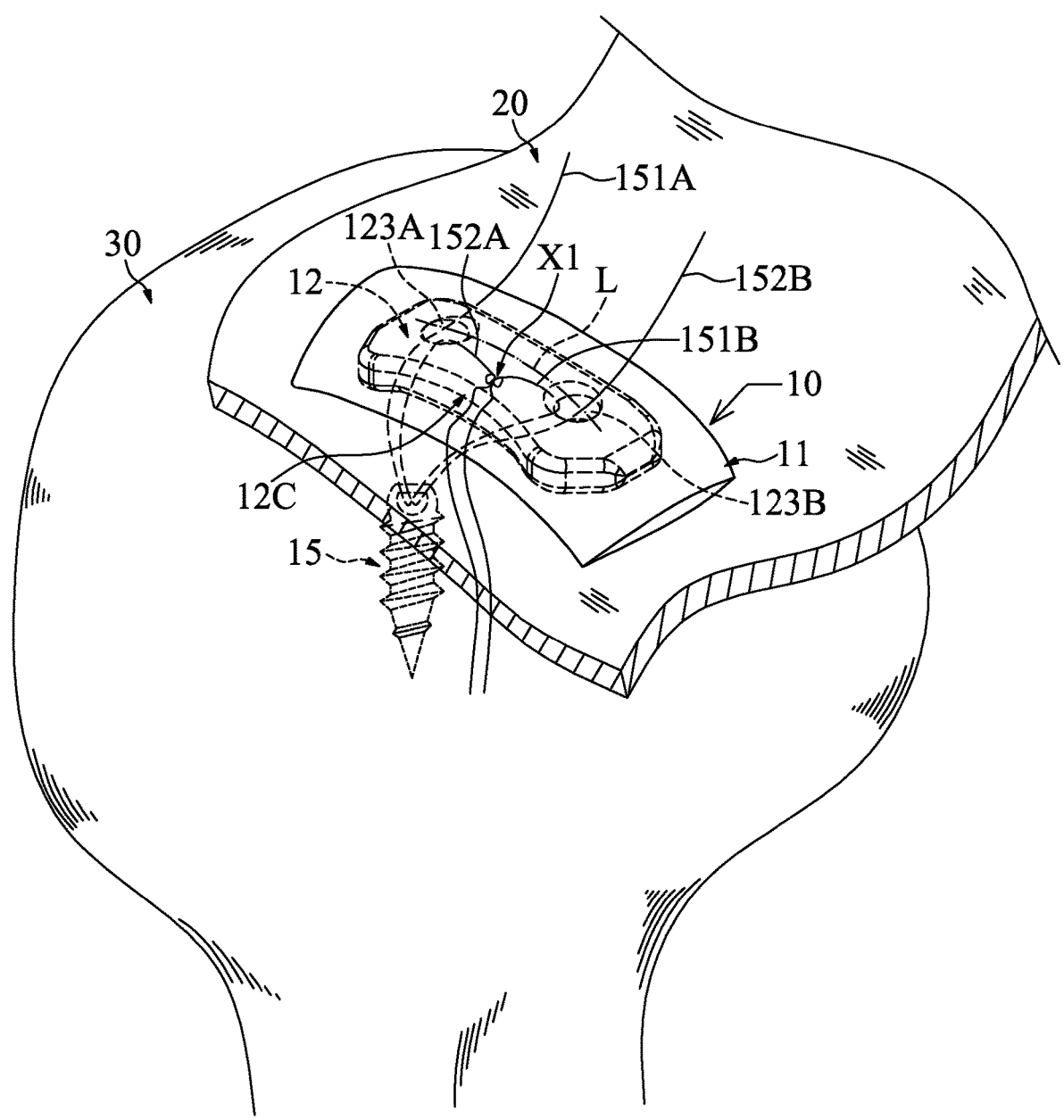

Referring to FIG. 2F, the second strand 151B and the third strand 152A are knotted to form a first strand node X1, and the first strand node X1 presses the bioinductive patch 10 and the detached tissue 20 tightly onto the hard tissue 30.

Figure 2G:
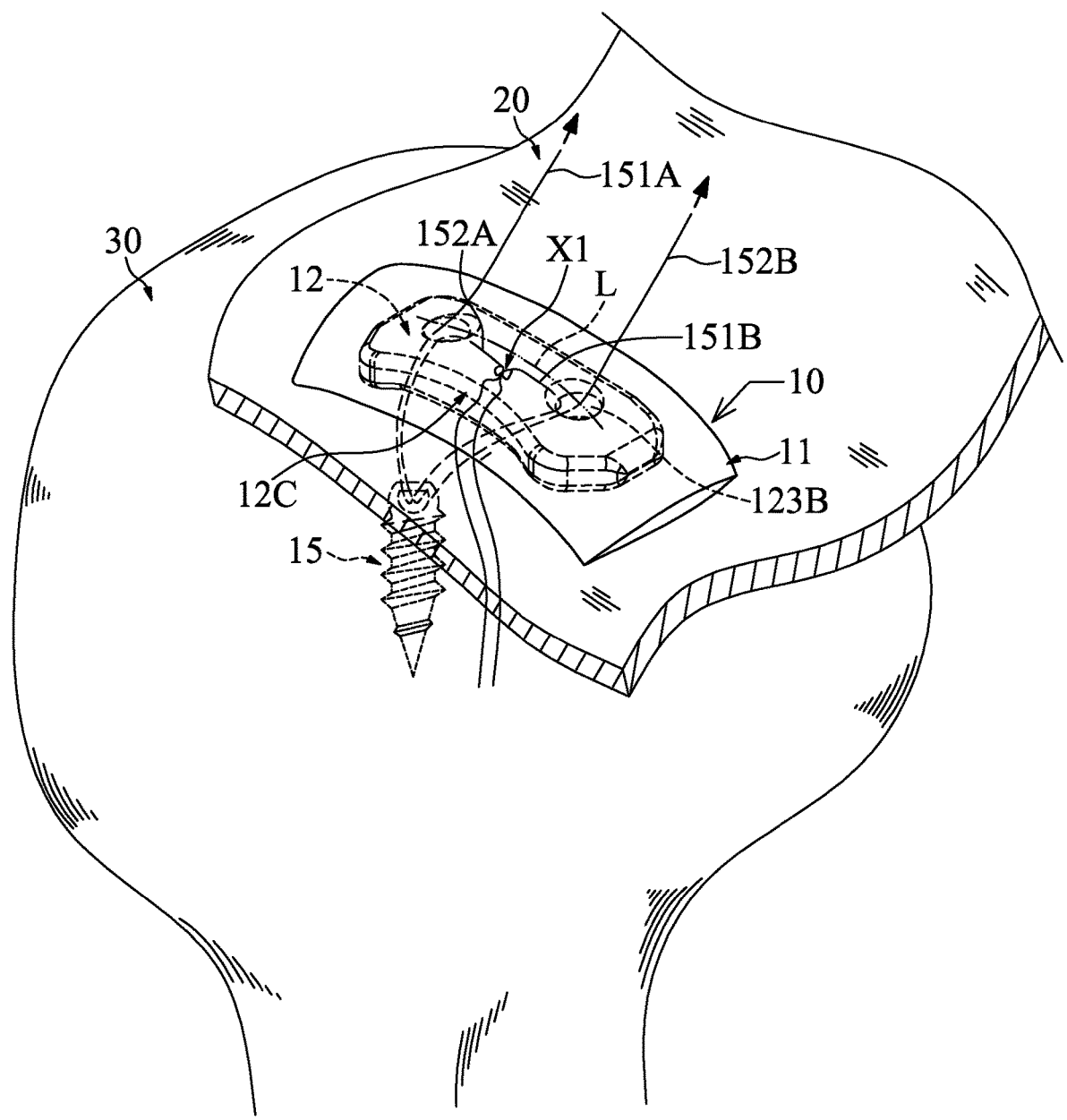

Referring to FIG. 2G, in some embodiments, the first strand 151A and the fourth strand 152B can be pulled to move the first strand node X1 onto the bioinductive patch 10, thereby enabling the first strand node X1 to press the bioinductive patch 10 and the detached tissue 20 more tight.

In order to prevent the detached tissue 20 from being damaged due to improper pressing, the first strand node X1 is located between the notch 12C and the centerline L to enable the bioinductive patch 10 to press the detached tissue 20 in a seesaw-like manner.

Figure 2H:
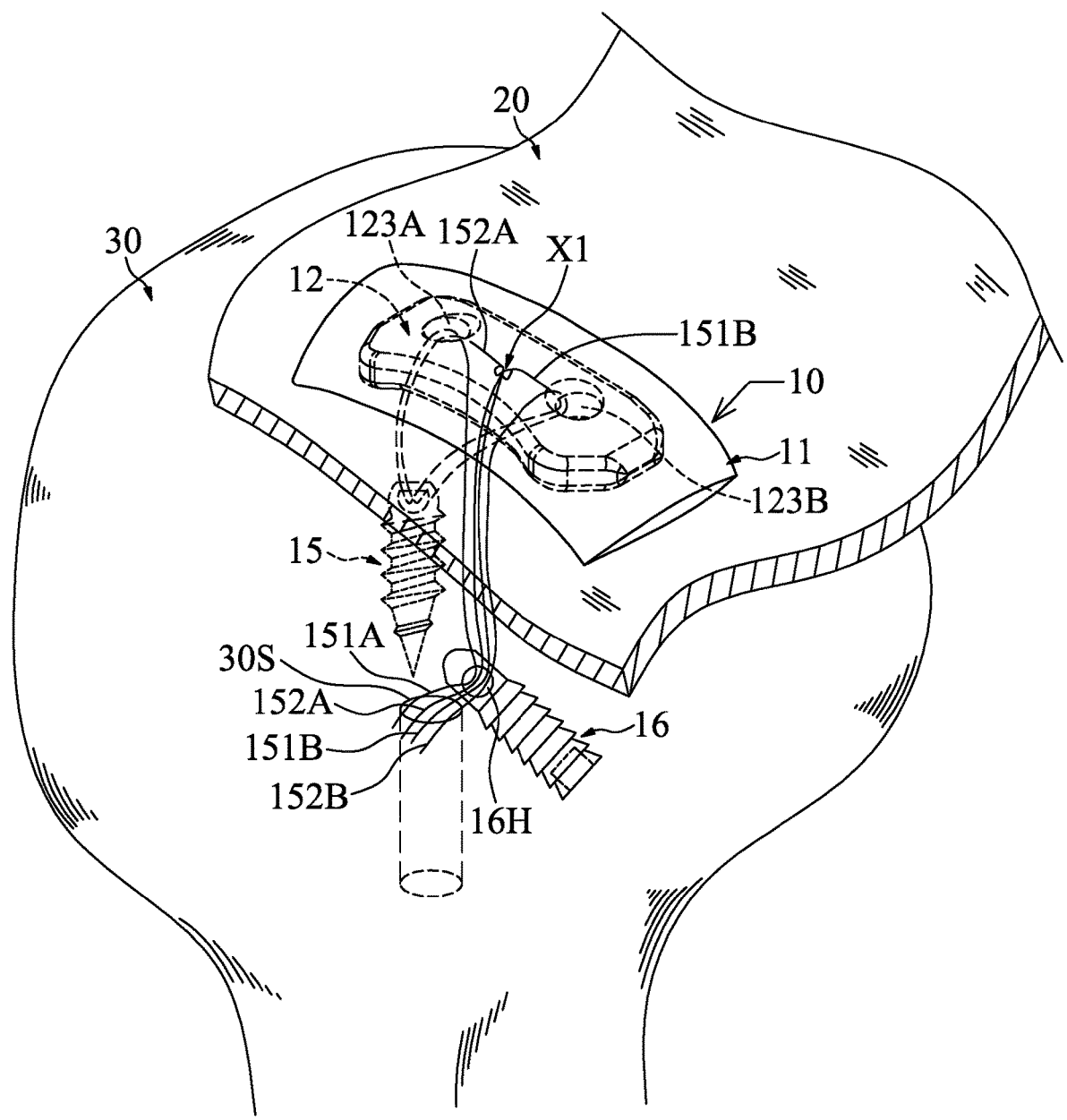

Referring to FIG. 2H, in some embodiments, the first strand 151A, the second strand 151B, the third strand 152A and the fourth strand 152B can be secured on a knotless anchor 16. The knotless anchor 16 has an islet hole 16H. The first strand 151A, the second strand 151B, the third strand 152A and the fourth strand 152B pass through the islet hole 16H.

Figure 2I:
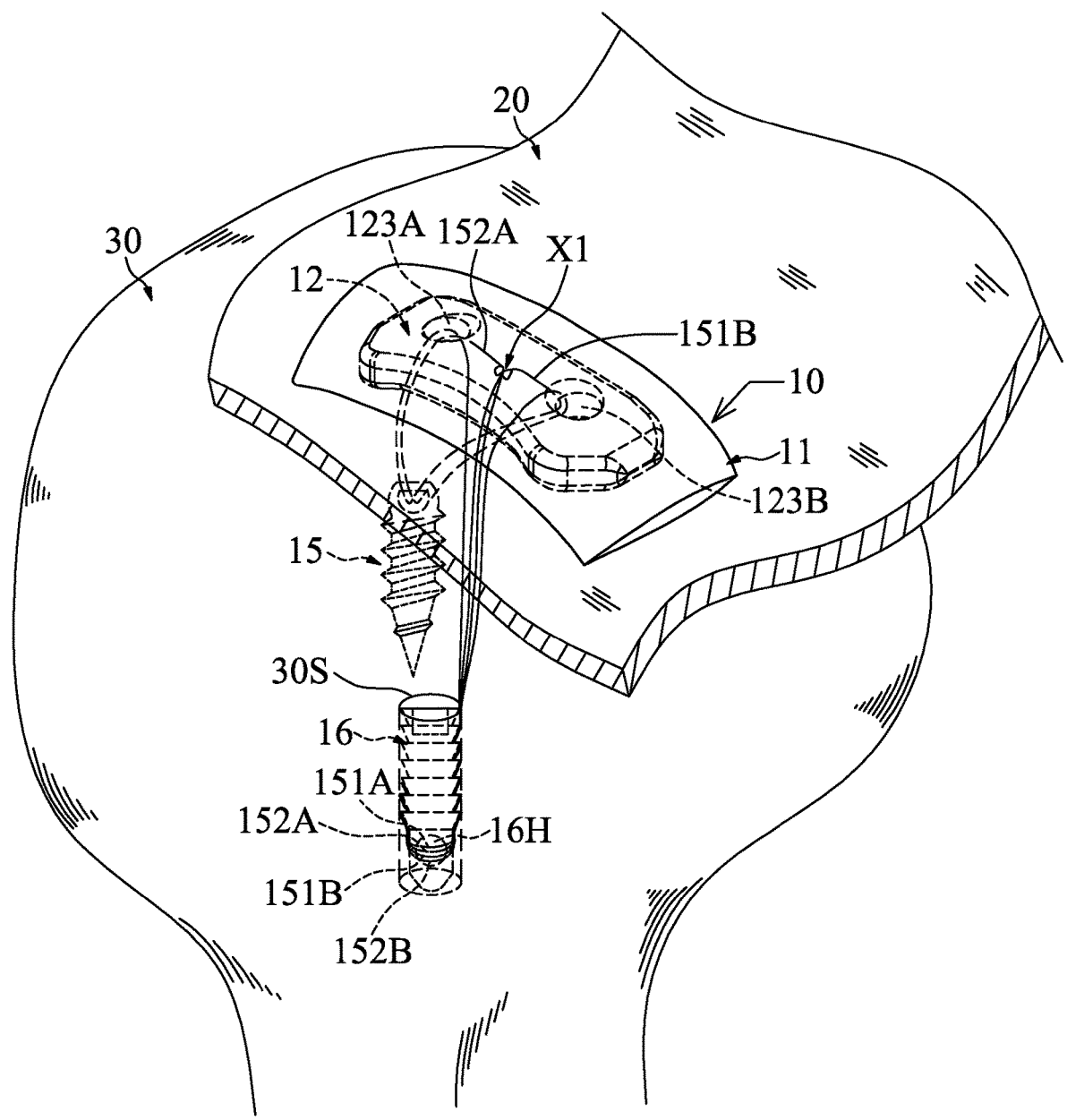

Referring to FIGS. 2H and 2I, the knotless anchor 16 is fixed on the hard tissue 30. In some embodiments, the hard tissue 30 has a pre-drilled socket 30S, and the knotless anchor 16 is fixed into the pre-drilled socket 30S.

Referring to FIG. 1O, in some embodiments, the first strand 151A and the fourth strand 152B are knotted to form a second strand node X2, and the second strand node X2 presses the bioinductive patch 10 and the detached tissue 20 tightly onto the hard tissue 30.

In order to prevent the detached tissue 20 from being damaged due to improper pressing, the second strand node X2 is located between the notch 12C and the centerline L to enable the bioinductive patch 10 to press the detached tissue 20 in a seesaw-like manner.

According to above operations, the bioinductive patch 10 of the present invention can effectively improve detached tissue-hard tissue healing and possess durable biological characteristics.

Moreover, the scope of the present application is not intended to be limited to the particular embodiments of the process, machine, manufacture, and composition of matter, means, methods and steps described in the specification. As those skilled in the art will readily appreciate form the present disclosure, processes, machines, manufacture, compositions of matter, means, methods, or steps, presently existing or later to be developed, that perform substantially the same function or achieve substantially the same result as the corresponding embodiments described herein may be utilized in accordance with some embodiments of the present disclosure.

Accordingly, the appended claims are intended to include within their scope such processes, machines, manufacture, and compositions of matter, means, methods or steps. In addition, each claim constitutes a separate embodiment, and the combination of various claims and embodiments are within the scope of the invention.

What is claimed is:

1. A method for reattaching a detached tissue to a hard tissue using a bioinductive patch, comprising:
    providing a suture anchor, wherein the suture anchor has a stitch hole, a first stitch and a second stitch, the first stitch passes through the stitch hole and divided into a first strand and a second strand, and the second stitch passes through the stitch hole and divided into a third strand and a fourth strand;
    fixing the suture anchor on a hard tissue;
    passing the first strand, the second strand, the third strand and the fourth strand through a detached tissue;
    providing a bioinductive patch, wherein the bioinductive patch comprises a patch body and a button, the patch body has an inner space, the button is disposed in the inner space of the patch body, and the button has a first suture hole and a second suture hole spaced from each other;
    passing the first strand and the third strand through the patch body and the first suture hole of the button, and passing the second strand and the fourth strand through the patch body and the second suture hole of the button; and
    knotting the second strand and the third strand to form a first strand node, and the first strand node pressing the bioinductive patch and the detached tissue tightly onto the hard tissue.

2. The method of claim 1, further comprising pulling the first strand and the fourth strand to move the first strand node onto the bioinductive patch.

3. The method of claim 1, wherein the button has a notch and a centerline, the centerline passes through a center of the first suture hole and a center of the second suture hole, and the first strand node is located between the notch and the centerline.

4. The method of claim 1, further comprising knotting the first strand and the fourth strand to form a second strand node, wherein the second strand node presses the bioinductive patch and the detached tissue tightly onto the hard tissue.

5. The method of claim 4, wherein the button has a notch and a centerline, the centerline passes through a center of the first suture hole and a center of the second suture hole, and the second strand node is located between the notch and the centerline.

6. The method of claim 1, further comprising securing the first strand, the second strand, the third strand and the fourth strand on a knotless anchor.

7. The method of claim 6, wherein the knotless anchor has an islet hole, and the first strand, the second strand, the third strand and the fourth strand pass through the islet hole.

8. The method of claim 6, further comprising fixing the knotless anchor on the hard tissue.

9. The method of claim 8, wherein the hard tissue has a pre-drilled socket, and the knotless anchor is fixed into the pre-drilled socket.

10. The method of claim 1, wherein the button has a top surface contacting the patch body.

11. The method of claim 10, wherein the top surface is an arc surface.

12. The method of claim 10, wherein the button has a plurality of top cavities formed on the top surface.

13. The method of claim 12, wherein the top cavities are disposed with at least one growth factor.

14. The method of claim 1, wherein the button has a bottom surface contacting the patch body.

15. The method of claim 14, wherein the button has a plurality of bottom cavities formed on the bottom surface.

16. The method of claim 15, wherein the bottom cavities are disposed with at least one growth factor.

17. The method of claim 14, wherein the bottom surface comprises a level plane and two inclined planes, and the two inclined planes are located at two sides of the level plane, respectively.

18. The method of claim 1, wherein the button has a central portion and two side curved portions, and the two side curved portions are connected to two sides of the central portion, respectively.

19. The method of claim 18, wherein a center maximum thickness of the central portion is greater than or equal to a thickness of either of the two side curved portions.

\* \* \* \* \*